(12) United States Patent
    Siegel

(10) Patent No.:     US 9,226,874 B2
(45) Date of Patent:     Jan. 5, 2016

(54) PHARMACEUTICAL IDENTIFICATION

(75) Inventor: Sheryl E. Siegel, Weston, CT (US)

(73) Assignee: Purdue Pharma L.P., Stamford, CT (US)

(*) Notice: Subject to any disclaimer, the term of this patent is extended or adjusted under 35 U.S.C. 154(b) by 453 days.

(21) Appl. No.: 12/881,889

(22) Filed: Sep. 14, 2010

(65) Prior Publication Data

US 2011/0217243 A1     Sep. 8, 2011

Related U.S. Application Data

(63) Continuation of application No. 10/698,981, filed on Oct. 31, 2003.

(60) Provisional application No. 60/422,567, filed on Oct. 31, 2002.

(51) Int. Cl.
    *A61K 9/28*     (2006.01)
    *A61J 1/00*     (2006.01)

(52) U.S. Cl.
    CPC ............... *A61J 1/00* (2013.01); *A61J 2200/60* (2013.01); *A61J 2205/00* (2013.01); *A61J 2205/20* (2013.01); *A61J 2205/30* (2013.01); *A61J 2205/60* (2013.01); *B65D 2203/12* (2013.01)

(58) Field of Classification Search
    CPC ...... A61K 9/20; A61K 9/2022; A61K 9/2072
    USPC ................. 424/464, 441, 465, 474; 514/4; 436/181, 56, 106, 113
    See application file for complete search history.

(56) References Cited

U.S. PATENT DOCUMENTS

| | | | |
|---|---|---|---|
| 3,333,031 A * | 7/1967 | Vincent, Jr. et al. | ............. 264/15 |
| 3,804,282 A | 4/1974 | Komendowski | ................. 215/32 |
| 3,871,334 A | 3/1975 | Axelrod | ........................ 119/29.5 |
| 4,154,636 A | 5/1979 | Motoyama et al. | ........... 156/243 |
| 4,242,484 A | 12/1980 | Suzuki et al. | .................. 526/273 |
| 4,260,517 A | 4/1981 | Woodford et al. | |
| 4,277,024 A | 7/1981 | Spector | ........................... 239/36 |
| 4,278,658 A | 7/1981 | Hooper et al. | |
| 4,480,177 A | 10/1984 | Allen | ............................. 235/379 |
| 4,674,444 A | 6/1987 | Axelrod | ........................ 119/29.5 |
| 4,690,927 A | 9/1987 | Voss et al. | |
| 4,717,017 A | 1/1988 | Sprinkel | ........................ 206/264 |
| 4,762,493 A | 8/1988 | Anderson | ........................ 434/84 |

(Continued)

FOREIGN PATENT DOCUMENTS

| | | | |
|---|---|---|---|
| EP | 0706944 B1 | 8/1996 | ............. B65B 25/00 |
| WO | 9506249 | 3/1995 | ............. G01N 33/53 |

(Continued)

OTHER PUBLICATIONS

Bidlingmaier et al.,"Odour Defitnition, Odour Measuring and Odour Generation";Odour Emissions from Compost Plants—Dimensioning Values for Enclosed and Open Plants (2003).

(Continued)

*Primary Examiner* — Michael G Hartley
*Assistant Examiner* — Micah-Paul Young
(74) *Attorney, Agent, or Firm* — Davidson, Davidson & Kappel, LLC

(57) ABSTRACT

Disclosed are methods for marking a pharmaceutical product, container or pharmaceutical packaging system with a scent to establish the identity and/or source of the pharmaceutical.

25 Claims, 2 Drawing Sheets

(56) References Cited

U.S. PATENT DOCUMENTS

| | | | | |
|---|---|---|---|---|
| 4,818,348 | A | | 4/1989 | Stetter ............................ 204/1 |
| 4,884,435 | A | | 12/1989 | Ehara ............................. 73/23 |
| 4,893,253 | A | | 1/1990 | Lodder et al. ................... 702/28 |
| 4,990,381 | A | | 2/1991 | Holzner et al. ............... 428/35.3 |
| 5,071,770 | A | | 12/1991 | Kolesae, Jr. ................... 436/151 |
| 5,098,715 | A | * | 3/1992 | McCabe et al. ............... 424/479 |
| 5,177,994 | A | | 1/1993 | Moriizumi et al. .......... 73/23.34 |
| 5,238,915 | A | * | 8/1993 | Fuwa et al. ...................... 512/4 |
| 5,282,572 | A | | 2/1994 | Fuller ............................ 239/56 |
| 5,289,715 | A | | 3/1994 | Staples et al. ............... 73/24.01 |
| 5,409,839 | A | * | 4/1995 | Balestrieri et al. ............. 436/56 |
| 5,419,920 | A | * | 5/1995 | Masson et al. .................... 427/7 |
| 5,429,952 | A | | 7/1995 | Garner et al. ................. 436/518 |
| 5,494,681 | A | * | 2/1996 | Cuca et al. ................... 424/484 |
| 5,503,332 | A | | 4/1996 | Glenn ............................ 239/56 |
| 5,541,851 | A | | 7/1996 | Sato et al. .................... 364/497 |
| 5,605,230 | A | | 2/1997 | Marino, Jr. et al. .......... 206/534 |
| 5,639,470 | A | | 6/1997 | Ishibashi et al. |
| 5,675,070 | A | | 10/1997 | Gelperin ..................... 73/23.34 |
| 5,753,511 | A | | 5/1998 | Selinfreund .................. 436/20 |
| 5,760,394 | A | | 6/1998 | Welle ........................... 250/303 |
| 5,773,783 | A | * | 6/1998 | Bowerman ................ 219/117.1 |
| 5,776,713 | A | | 7/1998 | Garner et al. ............... 435/7.92 |
| 5,776,783 | A | * | 7/1998 | Kell ............................. 436/111 |
| 5,824,345 | A | | 10/1998 | Milstein ....................... 424/489 |
| 5,855,907 | A | | 1/1999 | Peyman et al. .............. 424/434 |
| 5,885,640 | A | | 3/1999 | Andersson ................... 426/316 |
| 5,897,910 | A | * | 4/1999 | Rosenberg et al. .......... 427/2.14 |
| 5,928,609 | A | | 7/1999 | Gibson et al. .................. 422/90 |
| 5,938,018 | A | | 8/1999 | Keaveney et al. ............ 206/261 |
| 5,942,444 | A | * | 8/1999 | Rittenburg et al. .......... 436/518 |
| 5,958,714 | A | | 9/1999 | Gordon et al. |
| 6,025,200 | A | | 2/2000 | Kaish et al. .................... 436/56 |
| 6,066,347 | A | | 5/2000 | Prasad et al. |
| 6,102,224 | A | | 8/2000 | Sun et al. ...................... 215/252 |
| 6,153,220 | A | | 11/2000 | Cumming et al. ............ 424/464 |
| 6,192,882 | B1 | * | 2/2001 | Gonda ...................... 128/203.21 |
| 6,240,668 | B1 | | 6/2001 | Clawson et al. ................ 40/665 |
| 6,248,377 | B1 | | 6/2001 | Levine ........................... 426/87 |
| 6,294,209 | B1 | | 9/2001 | Andersson et al. ........... 426/115 |
| 6,349,719 | B2 | | 2/2002 | Gonda ...................... 128/200.14 |

FOREIGN PATENT DOCUMENTS

| | | | |
|---|---|---|---|
| WO | 9945514 | 9/1999 | ............ G08B 15/02 |
| WO | 0134024 | 5/2001 | ................ A61B 5/00 |
| WO | 0158451 | 8/2001 | .......... A61K 31/485 |
| WO | 0222075 A2 | 3/2002 | |
| WO | 03030129 A2 | 4/2003 | |

OTHER PUBLICATIONS

R.E.Lacey et al., "Application of Electronic Noses in Measuring Biological Systems"; ASAE Meeting Presentation (1998).

J.Yinon, "Detection of Explosives by Electronic Noses"; Analytical Chemistry (2003), p. 99A-105A.

K.S. Suslick et al.,""Smell-Seeing" A New Approach to Artificial Olfacation"; School of Chemical Sciences, University of Illinois at Urbana-Champaign (2001).

F. Davide et al. "Virtual olfactory interfaces: electronic noses and olfactory displays", Communications Through Virtual Technology: Identity Community and Technology in the Internet Age (2003).

"Olfactory," web article from www.dpi.gld.gov.au/environment/1464.html.

Office Action issued in connection with corresponding U.S. Appl. No. 10/698,981 on Sep. 29, 2014.

* cited by examiner

PHARMACEUTICAL IDENTIFICATION

This application is a continuation of U.S. patent application Ser. No. 10/698,981, filed on Oct. 31, 2003, which claims priority from U.S. provisional application No. 60/422,567, filed on Oct. 31, 2002, the disclosures of both are hereby incorporated by reference in its their entirety.

FIELD OF INVENTION

The present invention relates to a method of marking pharmaceuticals by adding to the product, container or packaging system, a scent to establish the authenticity and/or source of the pharmaceutical.

BACKGROUND OF THE INVENTION

Authentic pharmaceuticals are vulnerable to being diverted from e.g., legal pathways of distribution, for reasons of abuse (e.g. stealing pills to get high or to maintain addiction) or for unauthorized distribution and illegal sale (e.g, selling pharmaceuticals for profit on the gray market). When pharmaceuticals are misused or abused, they potentially pose danger to those who choose to use them in a manner other than as directed by a physician.

When law enforcement intercepts these diverted products, it may be difficult to determine their origin since they may not be in their original packaging. When a product is diverted, it is important to be able to identify/trace its origin in order to investigate and remedy the breakdown in integrity. A diffuse investigation wastes both time and resources (e.g. conducting searches of one factory, when the breech is in another factory). A delay in remedying the source of the diversion and/or counterfeiting can create more economic and personal harm. Remedying the problem quickly may serve to prevent further unintentional or intentional risk from misuse or abuse. Being able to authenticate the product and trace its manufacturing source may help to identify a breech in integrity quickly and efficiently.

Many pharmaceuticals are vulnerable to counterfeiting and false liability based on product substitution. After customers have acquired trust in products provided with a particular visually distinctive appearance, the products become vulnerable to counterfeiting, since a visually distinctive appearance can be susceptible to being imitated. Typically, a counterfeit product is made to resemble the genuine product as closely as possible with a view to misleading the purchaser into believing that the genuine product is being bought. Patients, pharmacists, wholesalers, and manufacturers may not be able to determine that the product is a counterfeit. Customers buy the counterfeit product with the expectation that they are buying the genuine product, with potentially life-threatening consequences, since the counterfeit may not meet the governmentally approved standard of quality, by providing treatment that is excessively potent, sub-therapeutic, or non-therapeutic. Being able to authenticate a product would assure quality and reduce risk. A method for marking a pharmaceutical that is not easily imitated or counterfeited, would help to authenticate the product.

There exists a need in the art, for compositions and methods of marking a pharmaceutical in a safe and reliable manner other than one that identifies it visually. In an effort to reduce misuse, abuse and diversion, and to comply with a risk management program, a new method of authentication and sourcing is disclosed.

All documents cited herein are hereby incorporated by reference in their entireties for all purposes.

OBJECTS AND SUMMARY OF THE INVENTION

It is an object of the invention to provide a method for marking a pharmaceutical formulation so that it can be identified by use of an identifying means. The pharmaceutical formulation can be any pharmaceutical formulation that can benefit by such marking such as, e.g., a pharmaceutical formulation subject to counterfeiting, diversion and/or abuse. In one non-limiting embodiment, the pharmaceutical formulation is an opioid or non-opioid analgesic formulation.

It is a further object of certain embodiments of the present invention to provide a method for authenticating a pharmaceutical formulation by identifying the presence of a scent associated with the pharmaceutical formulation.

It is a further object of certain embodiments of the present invention to provide a packaged pharmaceutical formulation such that the formulation in the package can be identified by its scent.

It is a further object of certain embodiments of the present invention to provide a pharmaceutical packaging system comprising a scent that enables authentication of the pharmaceutical formulation contained therein.

It is a further object of certain embodiments of the present invention to provide a pharmaceutical formulation comprising a scent that enables authentication of the pharmaceutical formulation.

The above objects of the invention and others can be achieved by virtue of the present invention, which is directed in part to a method of marking a pharmaceutical product with a scent for such identification or authentication.

In certain embodiments, the present invention is directed to a method of providing a scent to a pharmaceutical packaging system containing a pharmaceutical formulation, such that the pharmaceutical formulation is identifiable by the inclusion of the scent.

In certain embodiments, the present invention is directed to a packaging system comprising a pharmaceutical formulation, the packaging system further comprising a scent or aroma that can be used to identify the pharmaceutical formulation.

In certain embodiments, the present invention is directed to a pharmaceutical packaging system comprising a scent releasant. In certain preferred embodiments, the scent releasant is activated to release the scent each time the package is opened.

In certain embodiments, the present invention is directed to a method for identifying a pharmaceutical product comprising detecting a scent imparted to a pharmaceutical container containing a pharmaceutical formulation.

In certain embodiments, the present invention is directed to a method for providing for the identification a pharmaceutical product comprising imparting a scent to a pharmaceutical container containing a pharmaceutical product, the scent indicating the identity or source of the pharmaceutical product.

In certain embodiments, the present invention is directed to a method for providing for the identification a pharmaceutical product comprising imparting a scent to a pharmaceutical container adapted for containing a pharmaceutical product, the scent indicating the identity or source of the pharmaceutical product; and depositing the pharmaceutical product into the pharmaceutical container.

In certain embodiments, the present invention is directed to a method for identifying a pharmaceutical product comprising detecting prior to administration with an olfactory measuring device, a scent imparted to a pharmaceutical formulation.

In certain embodiments, the present invention is directed to a method for identifying a pharmaceutical product comprising detecting prior to administration with a non-human mammal, preferably a canine, a scent imparted to a pharmaceutical formulation.

In certain embodiments, the present invention is directed to a pharmaceutical packaging system comprising a scent releasant means in the form of a reservoir from which the scent is released each time the reservoir is activated. The scent releasant means is preferably activated by the mechanics of opening the pharmaceutical packaging system and the scent is then released. In certain embodiments, when the packaging system is closed, the scent releasant is preferably de-activated and scent release is decreased or terminated.

In certain embodiments of the present invention, the packaging system comprises a pharmaceutical formulation containment portion; a pharmaceutical formulation closure portion (e.g., a cap), wherein the closure portion is removed from the containment portion to gain access to a pharmaceutical formulation that is to be contained therein; and a scent releasant means. For example, the scent releasant means can have a peel seal in contact with the containment portion and the closure portion, wherein the peel seal seals the scent in a scent reservoir. When the closure portion is removed from the containment portion, the peel seal peels away from, or otherwise makes accessible to the atmosphere, the scent reservoir and releases the scent or allows it to volatilize into the air. Upon closure of the package, the peel seal reseals the reservoir preventing or minimizing further release or volatilization of the scent.

In certain embodiments, the scent for use in the present invention is in a quantity that is physiologically difficult, preferably physiologically impossible, to perceive by the human sense of smell, but which is sufficient to either be perceived by a non-human animal such as a scent-trained canine, or detected by an olfactory measuring device capable of identifying the scent emitted. For example, in certain embodiments, the amount of scent included in the pharmaceutical formulation and/or packaging system can be determined using the human olfactory threshold of a scent as described in M. Devos, et al., *Standardized Human Olfactory Thresholds,* 1990, the disclosure of which is hereby incorporated by reference.

In certain embodiments, the pharmaceutical formulation or pharmaceutical packaging system comprises the scent in sequestered form. In such embodiments, the scent is preferably not detectable unless the integrity of the pharmaceutical dosage form, or the integrity of the pharmaceutical packaging system, is compromised. In certain embodiments, "compromising the integrity of the pharmaceutical dosage form" includes crushing the dosage form (e.g., with a mortar and pestle), thereby allowing the scent to be released, or to be released in a detectable quantity. In certain further embodiments, "compromising the integrity of the pharmaceutical packaging system" includes, for example, opening (e.g., cutting or tearing open) the packaging system.

In certain preferred embodiments, the present invention is directed to a method of preventing counterfeiting of a pharmaceutical formulation comprising preparing, marketing, and/or distributing in commercial channels a pharmaceutical formulation as disclosed herein.

In certain preferred embodiments, the present invention is further direct to a method of preventing diversion of a pharmaceutical formulation comprising preparing, marketing, and/or distributing in commercial channels a pharmaceutical formulation as disclosed herein.

In certain embodiments, the present invention is further directed to a method of providing a marker to a pharmaceutical product that can distinguish between different batches of the pharmaceutical product, comprising adding one or more different scents (i.e., a "scent profile") to different batches of the pharmaceutical product to indicate the particular date or location of manufacture of the pharmaceutical product, wherein the scent is added either to a pharmaceutical product or to a pharmaceutical packaging system containing the product. For example, the inclusion of a plurality of scents in a pharmaceutical product or packaging can increase the complexity, and thus the informational content, in the scent profile of that product, thereby allowing a determination, e.g., of product source, manufacturing date, batch number, etc, of the scent profile.

In certain further embodiments, in addition to the one or more scents, one or more additional identifiers or authenticators are included in the pharmaceutical formulation and/or packaging system. In certain preferred embodiments, in addition to the scent(s), the pharmaceutical formulation or packaging system further comprises an additional marker such as a hapten or plurality of haptens to provide for the further identification or authentication of the pharmaceutical formulation. In certain preferred embodiments, the additional marker may be a hapten covalently bound to a chemical compound in the pharmaceutical formulation or the pharmaceutical packaging system. In certain preferred embodiments, the additional marker has a detectable physical characteristic such as, e.g., color, weight, density, magnetic attraction, luminescence, fluorescence, absorbance, chemical reactivity, or various characteristics detectable by optical methods known in the art. In certain embodiments, the use of different scents, or different markers in addition to a scent, can provide different bits of information. For example, a first scent in the formulation, container, and/or packaging can be an indicator of source, while a second scent in the formulation, container, and or packaging can be an indicator of the batch.

In certain embodiments, the invention is directed to a method for marking a pharmaceutical formulation comprising imparting a scent to a pharmaceutical product; the scent being undetectable by the human sense of smell, but detectable by a non-human animal or an olfactory measuring device, and the scent indicating the identity of the pharmaceutical product, the source of the pharmaceutical product, or a combination thereof.

In certain embodiments, the invention is directed to a method for marking a pharmaceutical formulation comprising imparting a scent to a pharmaceutical container adapted to contain a pharmaceutical product; the scent being undetectable by the human sense of smell, but detectable by a non-human animal or an olfactory measuring device, and the scent indicating the identity of the pharmaceutical product, the source of the pharmaceutical product, or a combination thereof.

In certain embodiments, the invention is directed to a method of identifying a pharmaceutical formulation comprising varying the identity of a scent imparted to the pharmaceutical formulation; the scent being varied by the manufacturer of the formulation according to a predetermined schedule to indicate when and/or where the pharmaceutical formulation was manufactured, bottled or packaged.

In certain embodiments, the invention is directed to a method for conducting a pharmaceutical business, comprising a) manufacturing a pharmaceutical product, kit or packaging system as disclosed herein; and b) marketing to healthcare providers the benefits of using the pharmaceutical product, kit or packaging system to deter counterfeiting, diversion or theft of the pharmaceutical product.

In certain embodiments, the invention is directed to a method for conducting a pharmaceutical business, comprising a) manufacturing a pharmaceutical product, kit or packaging system as disclosed herein; and b) informing a law enforcement agency of the benefits of using the pharmaceutical product, kit or packaging system to deter counterfeiting, diversion or theft of the pharmaceutical product. This method may further comprise providing the law enforcement agency with detection equipment for analyzing the scent profile of the seized pharmaceutical product to determine its authenticity, source, etc.

In certain embodiments, the invention is directed to a method for conducting a pharmaceutical business, comprising a) providing a distribution network for selling a pharmaceutical product or kit disclosed herein; and b) providing instruction material to patients or physicians for identifying the source of the pharmaceutical product or kit.

In certain embodiments, the invention is directed to a method for conducting a pharmaceutical business, comprising a) providing a distribution network for selling a pharmaceutical product or kit as disclosed herein; and b) providing instruction material to a law enforcement agency for identifying the source of the pharmaceutical product or kit. This method may further comprise providing the law enforcement agency with detection equipment for analyzing the scent profile of the seized pharmaceutical product to determine its authenticity, source, etc.

In certain embodiments, the invention is directed to a method for marking a pharmaceutical product for identification, comprising: identifying a pharmaceutical product containing an active ingredient that has been approved by a governmental agency for distribution and sale to the public; and imparting a scent to the pharmaceutical product in an amount that does not require reapproval by the governmental agency of the pharmaceutical product reformulated to include the scent; wherein the scent indicates the identity, source, or combination thereof of the pharmaceutical product.

In certain embodiments, the invention is directed to a method for marking a pharmaceutical product for identification, comprising: imparting a first scent to a pharmaceutical product and a second scent to a container for the pharmaceutical product; the first and second scents providing an indication of the identity, source, or combination thereof of the pharmaceutical product.

In certain embodiments, the invention is directed to a method for marking a pharmaceutical product for identification, comprising: imparting a first scent to a pharmaceutical product and a second scent to a packaging system for the pharmaceutical product; the first and second scent providing an indication of the identity, source, or combination thereof of the pharmaceutical product.

In certain embodiments, the invention is directed to a method of reducing diversion of a pharmaceutical formulation comprising imparting a scent to a pharmaceutical product in an amount which is below the human olfactory threshold; the scent being detectable by an olfactory device or a non-human mammal.

In certain embodiments, the invention is directed to a method of reducing preventing pharmaceutical drug counterfeiting comprising; imparting a scent to a pharmaceutical product, a container for the pharmaceutical product, packaging for the pharmaceutical product, or combination thereof; the scent imparted in an amount that is undetectable to the human sense of smell; the scent being detectable by an olfactory device or a non-human mammal such as, e.g., a canine.

In other embodiments, the invention is directed to a method of analyzing whether a pharmaceutical product is counterfeit comprising testing a pharmaceutical product with an unknown identity or source for the presence of a scent that is the same as that of an authentic pharmaceutical product. In such embodiments, the absence of the scent is indicative of a counterfeit product and the presence of the scent is indicative of an authentic product.

Preferably, the present invention is useful in authenticating the pharmaceutical formulation, or preventing diversion of the pharmaceutical formulation, or tracking the distribution of the pharmaceutical formulation, or determining the source of the pharmaceutical formulation, or determining the specific batch of the pharmaceutical formulation, and/or determining the date of manufacture of the pharmaceutical formulation, or a combination thereof.

For purposes of the present invention, the term "marking a product for identification" means associating a specific scent with a product so that the authenticity, source, identity or other information about the product can be determined. The scent, particularly in the concentration used, should be non-deleterious to the product, and preferably should not already be associated with the product.

For purposes of the present invention the terms "aroma", "scent", "odor", or "smell" may be used interchangeably.

For purposes of the present invention the terms "pharmaceutical formulation" and "pharmaceutical product" may be used interchangeably.

The term "scent profile" for purposes of the present invention means the particular scent or scents that are used to indicate the identity, source, or other information of the pharmaceutical product, container or package. The scent profile can be compared to a scent "fingerprint." For example, the "scent profile" can be the particular peak or peaks which are present when a composition of the present invention is tested with an olfactory measuring device.

The term "pharmaceutical formulation" or "pharmaceutical product" for purposes of the present invention means a drug composition which has received approval by a governmental authority (e.g., the Food and Drug Administration of the United States) to be safe and efficacious in human subjects.

The term "varying a scent" for purposes of the present invention means changing the scent used in the formulation, container, and/or packaging system. For example, varying a scent in the pharmaceutical formulation means that if one month the pharmaceutical formulation has, for example, an apple scent, then the next month the scent in the pharmaceutical formulation is changed to, for example, an orange scent. Alternatively, "varying a scent" means changing the same scent, for example, varying the potency of an orange scent, from, e.g., month to month.

For purposes of the present invention the term "method for providing for the indentification of" includes adding a marker to a pharmaceutical product, container, and/or pharmaceutical packaging system in order to allow for the product, container and/or packaging system to be identified for that marker.

For purposes of the present invention, the term "opioid agonist" is interchangeable with the term "opioid" or "opioid analgesic" and include both a single opioid agonist and combinations of more than one opioid agonist, and also include the base of the opioid, mixed agonist-antagonists, partial agonists, pharmaceutically acceptable salts thereof, stereoisomers thereof, ethers and esters thereof, and mixtures thereof.

DETAILED DESCRIPTION OF THE INVENTION

Figure 1:
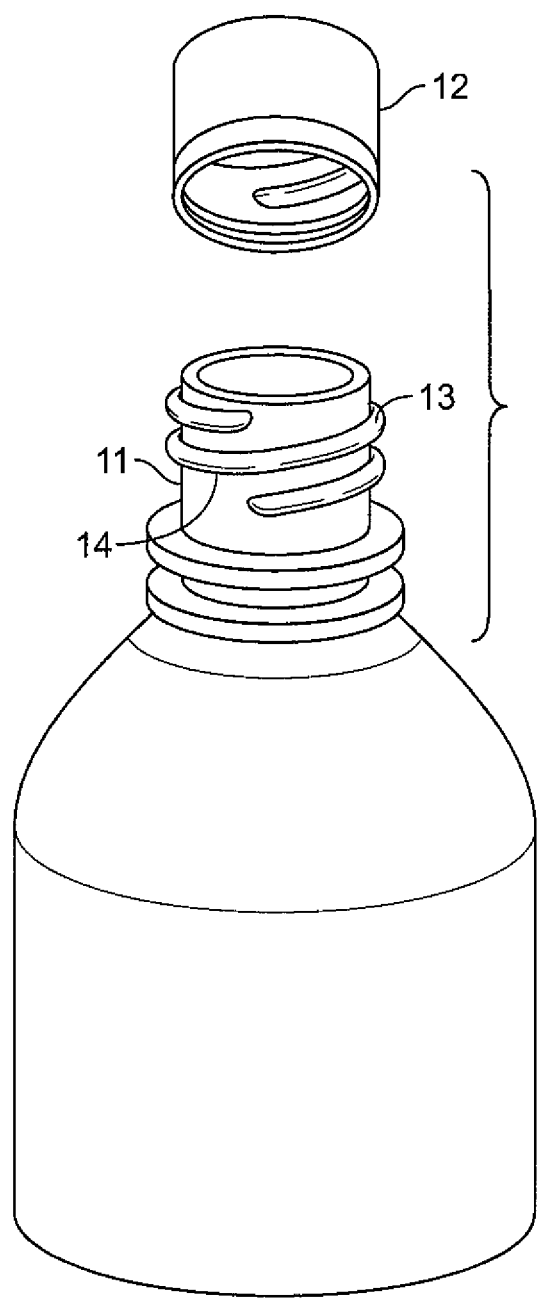
FIG. 1 depicts a pharmaceutical container including a scent in accordance with the present invention.

The present invention provides for a method to authenticate a pharmaceutical formulation, and/or to identify its source of distribution or its site of manufacture, by imbuing the pharmaceutical formulation, container or packaging material with a scent. Scent markers can involve smell recognizable factors, perfumed or otherwise scented members, "scratch and sniff" members, mixtures thereof and the like.

The scent for use in the present invention may be applied to, or incorporated into, the pharmaceutical formulation itself, or the container apparatus (e.g., bottle) containing the pharmaceutical formulation, or the box or other pharmaceutical packaging system containing the container, and combinations thereof. Alternatively or additionally, a scent releasant comprising a scent may be attached to the container containing the pharmaceutical, or to the box or other pharmaceutical packaging system, or to a combination thereof.

The inclusion of the scent of the present invention may be useful to provide the user, dispenser and/or law enforcement personnel of the pharmaceutical formulation with confirmation that the formulation being tested is the genuine pharmaceutical formulation from the correct source. In certain preferred embodiments, the scent is useful to provide law enforcement officials, border patrol police, and the like, with a way to authenticate and/or verify the pharmaceutical formulation "in the field", or conversely to detect counterfeit formulations.

In certain embodiments, where the scent is included in the pharmaceutical formulation, the scent is preferably applied directly to the pharmaceutical formulation via a standard coating process known in the art, e.g., via any appropriate spraying technique known in the art. For example, once the pharmaceutical formulation is encapsulated or tableted, then the capsule or tablet may be further coated with a scent useful for identifying the pharmaceutical formulation. In certain other embodiments, the scent is incorporated into the formulation during the tableting or encapsulation process. For example, the scent may be incorporated into the formulation, e.g., during granulation, during the coating process for bead formulations, during spheronization, applied after the aforementioned processes, in a combination of any of the aforementioned processes, and the like.

In certain preferred embodiments, when the scent is included in the pharmaceutical formulation, the scent is included in a coating on the formulation. In certain other embodiments, the scent is included in an intermediate coating of the pharmaceutical formulation and/or in a film coating on the final pharmaceutical formulation. For example, the scent may be included in a coating such as Opadry® (Colorcon, Inc.). Alternatively, the scent can be included in e.g., a solution used in the manufacturing of the formulation, e.g., during granulation or spray coating.

Preferably, when the scent is included in the pharmaceutical formulation, the scent is in the pharmaceutical formulation in an amount of below about 0.1% of the final formulation. In preferred embodiments, the scent is included in an amount of less than 100 ppm, less than 50 ppm, less than 25 ppm, less than 10 ppm or less than 5 ppm of the final formulation. In certain preferred embodiments where the scent is added to a pharmaceutical formulation which has already been approved by a governmental agency that regulates pharmaceuticals (such as, for example, the Food and Drug Administration of the United States of America), the scent is included in an amount (e.g., such as an allowable impurity amount) which would not require a re-filing with, or re-approval by, the governmental agency of the pharmaceutical product that has been reformulated to include the scent.

In certain embodiments, where the scent and the active ingredient of the pharmaceutical formulation are incompatible, the scent does not come in contact with the active ingredient of the pharmaceutical formulation during the process of manufacturing the pharmaceutical formulation and/or in the final pharmaceutical formulation.

In certain embodiments, where the scent is included in the pharmaceutical formulation, the scent is in a sequestered form. The scent can be sequestered using any know process such as, e.g., the process disclosed in PCT Publication WO 01/58451, the disclosure of which is hereby incorporated by reference. In embodiments where the scent is sequestered, the scent is preferably not substantially released unless the integrity of the pharmaceutical formulation is compromised. The integrity of the pharmaceutical formulation can be compromised by crushing the dosage form.

In certain embodiments, the present invention is directed to a pharmaceutical formulation comprising an active agent, and a sequestered scent indicating the identity or source of the pharmaceutical formulation, wherein the scent is detectable to a human olfactory system when the integrity of the pharmaceutical formulation is compromised. Alternatively, the present invention is directed to a pharmaceutical formulation comprising an active agent and a sequestered scent indicating the identity or source of the pharmaceutical formulation, wherein the scent is undetectable to a human olfactory system when the integrity of the pharmaceutical formulation is compromised, but is detectable either by a non-human animal (e.g., a canine) or by an olfactory measuring device when the integrity of the pharmaceutical formulation is compromised.

In certain preferred embodiments, when the scent is in sequestered form, the scent is included in multiparticulates, wherein the multiparticulates are individually coated with a material that substantially prevents release of the scent until the muliparticulates are dissolved or crushed. The multiparticulates may be incorporated into a pharmaceutical formulation with an active agent, e.g., into a tablet or a capsule.

In certain other embodiments, the scent in sequestered form is dispersed in a matrix comprising a material which substantially prevents the release of the scent. The matrix may be incorporated into a pharmaceutical formulation with an active agent, e.g., into a tablet or a capsule.

Sequestering materials for use in accordance with the present invention include those materials disclosed, among other places, in PCT Publication WO 01/58451. In certain preferred embodiments, a scent in sequestered form may be prepared by combining the scent with one or more pharmaceutically acceptable hydrophobic materials. For example, particles comprising the scent may be coated with a hydrophobic coating that sequesters the scent. Another example would be a scent that is dispersed in a matrix that sequesters the scent. In other embodiments, the scent can be sequestered in a matrix, with the sequestration augmented with the use of a coating over the matrix.

In certain embodiments directed to a sequestered scent, compromising the integrity of the formulation can provide a "burst" effect. This can facilitate the detection of the scent, e.g., by a human olfactory system, a non-human mammalian animal, or an olfactory measuring device, or a combination thereof. This may also provide a pharmaceutical formulation that hinders counterfeiting since it would be more difficult for a counterfeiter to recreate the "burst" effect of the formulation. In other embodiments, the scent is released from a pharmaceutical formulation in a controlled, prolonged, and/or gradual release.

In certain further embodiments, where the scent is included in the container containing the pharmaceutical formulation, the scent may be incorporated into the container during the manufacturing process of the container, and/or the scent may be applied to the inner and/or outer portions of the container. According to this embodiment, the container may take any appropriate form. Preferably, the container has a closure portion that is integral to the container, or that can be removable from the container. In certain preferred embodiments, the container is a bottle having a neck including an open top, and a closure portion that is rotatably affixed (e.g., a screw-on or child-proof cap) onto the neck of the bottle. In certain embodiments, the scent is release when the container is opened.

In certain embodiments, the wall of the container comprises a substrate (e.g., nylon) that has been impregnated with a scent, which can be prepared by immersing the container in an aqueous solution containing the scent for a time period sufficient to allow the scent to be absorbed by the substrate. The aroma component can subsequently be released by simple handling of the bottle. Examples of such odor-impregnating techniques are disclosed, among other places, in U.S. Pat. Nos. 3,871,334 and 4,674,444, the disclosures of which are hereby incorporated by reference. In another embodiment, the scent-producing component can be added to, and uniformly distributed throughout, a container (e.g., a polyurethane container) during the initial manufacture of the container.

In certain preferred embodiments, the scent is released from the container through the use of a scent releasant means, which preferably contains at least one scent useful as a marker according to the present invention. The scent releasant may be, for example and without limitation, a scented adhesive, a scent patch, a scent burst film, a scent dispensing tab, a scent containing capsule, a microencapsulated scent, a film of microencapsulated scent, or a combination thereof.

In certain embodiments, the scent releasant comprises an absorbent substrate in which the scent or scent source is stored in a volatile composition to be released when the container is opened. The absorbent preferably acts as a reservoir to retain the volatile scent composition, and releases a portion of the volatile scent composition each time the reservoir is exposed upon opening of the container. In certain preferred embodiments, the scent is released by tearing or stretching the absorbant substrate to release the scent.

In certain embodiments, the scent-containing substrate is in the form of an aroma strip which is covered by a re-sealable film, such that each time the film is pulled back from the strip (e.g., by opening the container), the strip releases the volatile scent, and scent release is subsequently stopped or minimized by re-applying the film to the strip. In certain embodiments, the scent is released by tearing or stretching the film until the film becomes perforated. Preferably the film has associated, re-sealable, pressure sensitive adhesive to ensure that the strip is resealed upon each closure of the container.

In certain embodiments the scent releasant can be a scent-dispensing tab that may be applied to the container or included in the container. For example, the tab may be in the form of a sac constituted by a base having a perforated dome marginally secured thereto to define a vented chamber occupied by an absorbent pad saturated by a liquid scent. The tab preferably has a layer of a pressure-sensitive adhesive allowing attachment of the tab to the container containing the pharmaceutical formulation.

In certain preferred embodiments, the scent releasant is a layer of microencapsulated scent material containing scent microcapsules, and is secured to at least one of the top or closure portion of the container. When the closure portion is rotated on the neck of the container for removal from the top to open the container so that the pharmaceutical product is dispensed therefrom, at least some of the aroma capsules are ruptured and the scent is released.

Microencapsulation is a process in which very thin coatings of inert natural or synthetic polymeric materials are deposited around microsized particles of solids, droplets of liquids, or gas. Products formed are known as microcapsules. Microcapsules typically consist of two major parts (i.e., the inner part and the outer part). The inner part is the core material comprised of one or more active ingredients. In accordance with the present invention, the active ingredient for encapsulation is one or more of the scents described herein. These active ingredients may be in the form of solids, liquids, or gases. The outer part is the coating material, which is preferably a high molecular weight polymer or a combination of such polymers. The coating material can be chosen from a number of natural and synthetic polymers. The coating material preferably is non-reactive with the core material, and is preferably biodegradable and nontoxic. Other components such as, for example, surfactants and plasticizers, may also be added to microcapsules.

The encapsulation may provide for the enhancement of the stability of the core material including the scent. For example, the encapsulation of a scent preferably protects the scent against atmospheric deterioration.

Preferably, the scent releasant described herein is in contact with the container. Preferably, the scent releasant releases a unique scent that can be associated with the pharmaceutical formulation contained in the container.

In certain embodiments, a label is provided on the outside of the container. The label may be applied to the outside of the container by an adhesive. In certain embodiments, the adhesive may contain the scent, the scent may be applied over the label, the label itself may contain the scent, or a combination of the aforementioned may be used. The label may further include some other identifying feature for the drug. Further, the label may comprise a package insert that provides details about the pharmaceutical formulation contained in the container and is applied to the container by an adhesive. Additionally, the scent area of the label or of the container may also be covered with a peel-off type cover to preserve the freshness of the scent during shipping and storage.

The label may simply be coated with a liquid solution containing scent-producing elements and then sealed with a protective coating. One method of applying scent producing elements to a label utilizes the method commercialized by Sandy Alexander, Inc., of Clifton, N.J., which employs a press varnish that may be directly applied to printing presses to enable the combination of high-quality color printing and scenting within an in-line operation. This process produces a label with an integrated scent area, and permits labels to be manufactured without an additional step. According to this process, the intensity of the scent can be controlled and the image printed on the sheet material does not have to be distorted or broken up to release the scent. Additionally, this process allows application in defined areas and can allow for multiple scents on a single sheet of material. This scent release is activatible a number of times, and requires no special paper or substrate so conventional substrates for labels are suitable.

In certain embodiments, the headspace of the container containing the pharmaceutical formulation is filled with a scent or aroma so that upon opening the container, the person opening the container can identify the pharmaceutical contained therein by the scent or aroma released therefrom.

The container having a scented headspace portion can be prepared by techniques known in the food packaging art. Systems for aromatizing headspace of a food package that may be used in accordance with the present invention are disclosed, among other places, in European Patent No. 0 706 944 and U.S. Pat. No. 5,885,640, the disclosures of which are hereby incorporated by reference in their entireties. Another technique includes providing a pharmaceutical container which defines a cavity for containing a pharmaceutical formulation; inserting a pharmaceutical formulation into the cavity; inserting a liquid mixture of a pharmaceutically acceptable scent composition liquid carrier into a portion of the container separate and apart from the cavity which contains the pharmaceutical formulation; removing the liquid carrier from the scent composition, preferably by evaporating the carrier, while leaving the scent composition preferably in a form of a residue, preferably comprising a solidified form, so that the scent is released from the container upon opening the container; and covering and sealing the container part with a cover part so that the pharmaceutical and scent composition are sealed and contained within the package separate and apart one from the other within separate package cavities and so that the cover part is removable and so that when the cover part is removed, the separate cavities are opened to the atmosphere releasing the scent.

In carrying out the process with a liquid carrier, so that removal of the carrier may be effected, the carrier is preferably selected from solvents having a boiling point at or lower than 100° C. at standard atmospheric pressure, which enables readily carrying out evaporation or volatilization of the carrier. Such solvents can be aqueous or organic and include, for example and without limitation, water, ethanol, methylformate, ethylformate, propanol, hexane, mixtures thereof, and the like. In preferred embodiments, the liquid solvent carrier is removed by pulling a vacuum so the solvent evaporates or vaporizes. Preferably the residue that remains is not visually perceptible, but is in a concentration or amount effective to provide the intended olfactory effect upon opening the package. In certain embodiments, the scent composition may also be present in an aerosol form or gaseous form rather than only as a residue.

Preferably, the scent composition is in an amount such that it is effectively available for olfactory response when the cover part is peeled off the container. In certain preferred embodiments, the cover part may be a web or sheet, or other known materials suitable for covering and sealing package bottles containing pharmaceutical formulations, such that the cover part is peelable and sealed to form a packaged body.

In certain embodiments, the amount of scent to be applied and/or incorporated into a container and/or pharmaceutical formulation will depend upon the smell intensity of the scent concentrate. Preferably the amount used is a sufficient amount to impart the desired scent (detectable or undetectable to humans) to the container such that the scent will be retained and not dissipate under normal storage. The scent preferably provides for the identification of the pharmaceutical formulation and/or source of the pharmaceutical formulation contained in the container or the packaging system. In certain embodiments, the scent provides for the ability to determine the manufacturing site of the pharmaceutical formulation, the specific batch of the pharmaceutical formulation, the date on which the pharmaceutical product was manufactured, or a combination thereof. In certain embodiments, the scent included in the pharmaceutical formulation and/or packaging system may be varied in order to prevent counterfeiters from producing the pharmaceutical formulations and/or packaging systems with the same scent. For example, the scent can be varied for every new pharmaceutical batch prepared, or every few months, or every one or two years, etc.

In certain embodiments, the container including the pharmaceutical formulation can be placed within a packaging system such as, e.g., a box. In certain embodiments, the packaging system includes a scent releasant as described herein. For example, when the packaging system is a box, the box preferably includes at least one flap defining a closure. The scent releasant can be included in the adhesive utilized for sealing the flap of the box or for securing indicia, e.g., a patient package insert, onto the box. The scent included in the adhesive preferably provides the ability to determine the manufacturing site of the pharmaceutical formulation, the specific batch of the pharmaceutical formulation, the date on which the pharmaceutical product was manufactured, or a combination thereof. Preferably, the scent is continuously released from the adhesive.

In another embodiment, the scent releasant can be a scent burst film disposed over the flap of the box. Preferably, the scent burst film is placed between two flaps of a closable package system, wherein the flaps are in overlapping opposing relationship and the scent burst film can be adhered between opposing overlapping flaps. In a preferred embodiment, the scent burst film includes a supporting base adhered to at least one flap of a package, a layer bonded to the outside face of the supporting base, the layer comprising, e.g., a vinyl plastisol resin containing a scent, and a flexible, continuous, smooth cover sheet covering the layer whereby the scent is retained for extended periods of time. The cover sheet is preferably adhered to the second overlapping flap of the package. Upon removal of the cover sheet (e.g., by removal of one of the overlapping flaps), the scent becomes immediately available and is gradually released.

In certain other embodiments, the scent releasant of the packaging system of the present invention is a separate scent compartment attached to the flap of the package. The compartment suitable for containing a scent is sealed with a removable cover. The scent is released when the removable cover of the compartment is removed.

In another embodiment, the scent compartment is a separate cavity formed into the flap, the cavity being sealed with a removable cover. The scent is releasable when the removable cover is removed.

In another embodiment, the scent releasant is a scent dispensing tab wrapped in a hermetically sealed foil package that prevents emission of the scent until the foil package is ruptured, wherein the foil packaging system can be adapted to adhere to at least one flap of the package or to the container described above. The scent-dispensing tab can be disposed on the interior or exterior of the flap (or container or container closure). The scent-dispensing tab can be a pad or wick saturated with a concentrated liquid scent that retains and releases the scent contained therein.

In another embodiment, the scent releasant can be an adhesive label on the container described above or the packaging system described above, the label being coated on its outer face with a thin film of microencapsulated scent, wherein the microencapsulated scent is covered by a protective coating whereby the scent is released by scratching off the protective coating, thereby disrupting the capsules containing the scent (e.g., such as a "scratch and sniff" formulation). In certain embodiments, the scent releasant of the packaging system or container apparatus is a scent-containing capsule breakable by hand pressure, wherein the capsule is secured to the exterior of the flap.

In certain preferred embodiments of the present invention, the scent is in an amount or concentration that is undetectable by the human sense of smell, but is detectable by the use of an electronic olfactory measuring device. The olfactory measuring device may be used, for example, by the user of the pharmaceutical product (e.g., the patient), the dispenser of pharmaceutical product, a person involved in the chain of distribution of the product, a law enforcement official, or the manufacturer of the product.

Suitable olfactory measuring devices include those described in, for example, U.S. Pat. Nos. 5,675,070 and 5,177,994, and those manufactured by Neotronics of Hertfordshire, Great Britain; ALPHA M.O.S., Inc. of DeMotte, Ind.; and Aromascan Inc. of Hollis, N.H.

In certain embodiments, the olfactory measuring device is known as an Electronic Nose. See H. T. Nagle, S. Schiffman and R. Guitierrez-Osuna, "The How and Why of Electronic Noses", IEEE Spectrum, pg. 22-33, September 1998. An electronic nose provides a recognizable visual image in N-dimensional space (where N equals the number of sensors) of specific vapor mixtures (fragrances) containing possibly hundreds of different chemical species. An electronic nose is designed to quantify and characterize scents. Sensors are selected for their chemical affinities, and chemi-sorbing polymer films are commonly used for this purpose. Many sensors can be used, and a serial polling of each sensor reading produces a histogram of sensor outputs, which comprises the olfactory response of the electronic nose. Certain "artificial noses" that may be used in accordance with the present invention include transducer arrays, the collective output signal of which correlates to the existence of a compound having a certain odor. Such artificial noses are described, among other places, in U.S. Pat. Nos. 4,818,348; 4,844,535; 5,071,770; 5,541,851; and 5,928,609. Electronic noses described in J. Yinon, Analytical Chemistry, "Detection of Explosives by Electronic Noses" (2003), may also be used in accordance with the present invention.

In certain embodiments, a method, apparatus and system as described in PCT Publication WO 02/22075 A2 may be used to compare the odor characters of liquid and gaseous fragrance materials based on a comparison of the optical absorption spectrum in the UV to the near IR associated therewith.

In certain embodiments, the olfactory measuring device is, or comprises, a gas chromatography device. See Robert L. Grobe, "Modern Practice of Gas Chromatography", John Wiley & Sons, copyright 1985 Part 1, Chapter 2, Theory of Gas Chromatography, pp. 50-114, to Separate the vapor into its individual chemical components and to obtain a chromatographic "scent profile". Common GC systems utilize long capillary columns many meters in length, and although analysis times may be long, they tend to be accurate and precise. A recent development has been the use of directly heated short chromatography columns, cooled sample traps, and focused surface acoustic wave (SAW) interferometric vapor detectors. See, e.g., U.S. Pat. No. 5,289,715. The SAW detector produces a variable frequency in response to analytes condensing upon and evaporating from the surface of a temperature controlled piezoelectric crystal.

In certain alternative embodiments, the olfactory measuring device includes JR, NMR and mass spectrometry devices.

In certain embodiments, the olfactory device is a handheld olfactory device, which is easily useable, e.g., by law enforcement individuals such as border police. Preferably, the olfactory device is designed to authenticate a particular pharmaceutical formulation based on detection of a scent (e.g., a covert scent) included in the pharmaceutical formulation and/or the pharmaceutical packaging system, and is designed to provide a simple "yes" or "no" answer. In certain preferred embodiments, the olfactory device is self-destructing when the device itself is tampered with in order to avoid the replication or tampering of the olfactory device or any software program installed in the olfactory device.

Scents for use in the present invention can be selected from any appropriate scents known in the art including, for example, any scent from the group consisting of volatile oils, synthetic flavor oils, flavoring aromatics, natural flavor oils, flavoring liquid oleoresins, flower extracts, fruit extracts, combinations thereof, and the like. In certain embodiments, the scent can be selected from the group consisting of aldehydes and esters such as benzaldehyde (cherry or almond), citral, i.e., alphacitral (lemon or lime), neral, i.e., beta-citral (lemon or lime), decanal (orange or lemon), aldehyde C-8 (citrus fruits), aldehyde C-9 (citrus fruits), aldehyde C-12 (citrus fruits), tolyl aldehyde (cherry or almond), 2-6-dimethyloctanal (green fruit), 2-dodecenal (citrus or mandarin) and mixtures thereof, and the like. Other scents that may be useful include, for example and without limitation, anise, apple, arnica, balm mint, banana, basil, black pine, caraway, carnation, chamomile, cherry, Chinese cedar wood, chocolate, cinnamon, coconut, coffee, cypress, dill weed, eucalyptus, fir, fleurier, florogenia, forest ground, fresh baked bread, ginger bread, green apple, green bean, green spruce, hay flower, hazel, honey, hyacinth, incense, jacilia, jasmine, juniper, keymi, lavender, leather, lemon, lilac, lotus, mandarin, mango, maracuja, marjoram, May-flower, menthol, mixed alpine herbs, mugol, northern birch, ocean breeze, orange, orchid, ozone pine, peach, pear, petunias, pine, pinewood, pink pepper, pizza, plum, rose, raspberry, rosemary, sandalwood, sea breeze, Siberian spruce, spring, spruce pine, strawberry, thyme, tobacco, tomato, valerian, vanilla, violet, waffle, wild woodberry, mixtures thereof, and the like. In certain embodiments a musk scent may be used.

In certain preferred embodiments, the scent is "generally recognized as safe" by the Flavor and Extract Manufacturer's Association. In certain preferred embodiments, the scent is, for example and without limitation, trans-anethole (1-methoxy-4-propenylbenzene)-anise; benzaldehyde (benzoic aldehyde)—bitter almond; butyl isobutyrate (n-butyl 2, methyl propanoate)—pineapple; cinnamaldehyde (3-phenylpropenal)—cinnamon; citral (2-trans-3,7-dimenthyl-2,6-octadiene-1-al)—citrus; menthol (1-methyl-4-isopropylcyclohexane-3-ol)—menthol; and alpha-pinene (2,6,6-trimethylbicyclo-(3,1,1)-2-heptene)—pine.

In certain other embodiments, the scent is selected from aliphatic fatty acids with short chains of two to six carbon atoms, such as acetic acid, propionic acid, isobutyric acid, isovaleric acid and isocaproic acid; ketones, such as α-ionone and 2-piperidone; aldehydes, such as 4-hydroxy-3-methoxy benzaldehyde; amines such as triethylamine; o- and p-hydroxy benzoic acids and their esters, in particular p-hydroxy benzoic acid, p-hydroxymethyl benzoate, p-hydroxyethyl benzoate and p-hydroxypropyl benzoate, and methyl salicylate (orthohydroxybenzoate); combinations thereof and the like.

Additional lists of odorous molecules identified by their molecular weight and their saturation vapor tension can be found in standard works such as "Handbook of Organic Chemistry", for example, and in specialized works in the field of olfaction, psychophysiology and animal behavior such as, for example, the series of works entitled "Chemical Signals in Vertebrates" Volumes 1-9, Kluwer Academic Publishers, 1977-2001.

In certain embodiments, Perfluorocarbon Tracer (PFT) technology as described in U.S. Pat. No. 5,409,839, the disclosure of which is hereby incorporated by reference, is used in accordance with the present invention. In such embodiments, the pharmaceutical product, container, and/or packaging system is includes a PFT that gives off a detectable tracer (e.g., vapor or scent), which can be detected by humans, a non-human, and/or an olfactory measuring device. Such PFT's include, for example and without limitation, perfluorocycloalkanes such as perfluorodimethylcyclobutane (PDCB), perfluoromethylcyclohexane (PMCH), and perfluorodimethylcyclohexane (PDCH); perfluoroaromatics such as hexafluorobenzene (HUB), octafluorotoluene (OFT), decafluorobinphenyl (DFBP), decafluoroxylene (DFX), octafluoronaphthalene (OFN), and pentafluoropyridene (PM, perfluoroalkanes such as perfluorohexane (PFH), perfluoropentane (PFPT), and perfluorooctane (PFO), and perfluorocycloalkenes such as decafluorocyclohexene (DFCH) and octafluorocyclopentene (OFCP), pf-methylcyclopentane (PMCP); pf-1,2-dimethylcyclohexane (o-PDCH$^1$); pf-1,3-dimethylcyclohexane (m-PDCH$^1$); pf-1,4-dimethylcyclohexane (p-PDCH$^1$); pf-trimethylcyclohexanes (PTCH); and combinations thereof. Certain preferred PFT's are PMCH, PMCP, o-PDCH$^1$, m-PDCH$^1$, p-PDCH$^1$ and PTCH.

In certain embodiments, the scent for use in the present invention is in a quantity that is perceivable by the human sense of smell. In certain alternate embodiments, in order to prevent counterfeiting of the aromas, and to provide a covert "scent profile" of the pharmaceutical product, the scent is in a quantity which is difficult to perceive or not perceivable by the human sense of smell, but which can be detected by other means.

For example, in certain embodiments the scent for use in the present invention is in a quantity that is physiologically difficult to perceive, preferably physiologically unperceivable, by the human sense of smell, but is in an amount that is sufficient either to be perceived by a non-human mammal (e.g., a canine) or detected by an olfactory measuring device capable of identifying the odor emitted. Preferably, the scent is known to be capable of being detected by a non-human mammal or by an olfactory measuring device (as disclosed above) at extremely low thresholds.

The sense of smell is much better developed in certain mammals, whether naturally or after training, than in human beings. By use of their sense of smell, these mammals can identify the identity or origin of even extremely tenuous or faint odors. In certain embodiments, it is sufficient to affix to the pharmaceutical product a specific scent known to be undetectable by the human sense of smell, but detectable by a given animal or olfactory measuring device. Dogs may be especially useful in accordance with carrying out the present invention, since a dog's sense of smell is up to a million times more sensitive than that of a human. In addition, there are certain odors that are particularly offensive to dogs, such as citrus smells (e.g., lemon, lime, and orange), spicy smells (e.g., red pepper) and citronella. Therefore, in certain embodiments, one or more of these scents are preferred, since they be more detectable by canines In certain preferred embodiments, the amount of scent used is in an extremely low concentration, and in particular, is in a concentration so that one skilled in the art may easily affix a carrier containing a scent to the object to be marked such that the carrier comprising the scent is imperceptible to the human eye.

In certain embodiments, the present invention is further directed to a method of varying or changing the scent for use in the present invention, preferably depending on the particular time and/or place that the pharmaceutical formulation was manufactured, bottled, or packaged. For example, if the pharmaceutical formulation was manufactured on a Monday, then the scent could be one specific odor or combination of odors (e.g., cherry, apple, combination thereof) giving a certain "scent profile" or "scent fingerprint"; if the pharmaceutical formulation was manufactured on a Tuesday, then the scent could be a different specific odor or combination of odors (e.g., chocolate, banana, combination thereof). In a preferred embodiment, the scent can be varied depending on the lot or batch number of the pharmaceutical formulation. For example, the scent incorporated into the pharmaceutical formulation; the container containing the pharmaceutical formulation; the box or other pharmaceutical packaging system containing the bottle or apparatus; combinations thereof; and the like, in one lot can be one odor or combination of odors (e.g., cherry, apple, combination thereof), while another lot can be another odor or combination of odors (e.g., chocolate, banana, combination thereof).

In certain preferred embodiments the present invention is further directed to a method of preventing diversion of a pharmaceutical formulation. For example, the inclusion of the scent in accordance with the present invention could be used to determine the source (e.g., the manufacturing plant or pharmaceutical distribution facility) of the pharmaceutical formulation. In view of the fact that the manufacturing and packaging of a pharmaceutical product can be carried out in different parts of a country and/or in multiple countries, the inclusion of different scents in the pharmaceutical product could provide the information necessary to indicate, e.g., which manufacturing facility was the source for the pharmaceutical. The inclusion of different scents in a pharmaceutical product could serve to indicate whether a product has been diverted from a proper consumer, client, or customer, to an improper consumer, client, or customer.

In certain preferred embodiments, the packaging system, container, or pharmaceutical formulation of the present invention can further include a visual indicator. A visual indicator can be, for example, a certain ink, dye, phosphorescent material, hologram, watermark, micro-replicated pattern, or a combination thereof.

In certain embodiments, a marker composed of a low molecular weight hapten may be covalently bound to an ingredient in the pharmaceutical formulation, a component in the container or pharmaceutical package, or combination thereof. Such markers are described, for example, in PCT Publication WO 95/06249, the disclosure of which is hereby incorporated by reference. In certain embodiments wherein a hapten is included, the marker can be produced by first covalently binding a hapten to a functional monomer, and then polymerizing the hapten-monomer compound to form a polymer having covalently-bound hapten. Thereafter, the polymer can be incorporated into the pharmaceutical dosage form, container, and/or the pharmaceutical package. The presence of the hapten marker can be detected as described in PCT Publication WO 95/06249.

The methods of the present invention can be used in accordance with any pharmaceutical formulations known in the art, and particularly those susceptible to theft, diversion, counterfeiting, and/or misuse or abuse. In certain preferred embodiments, the pharmaceutical formulation of the present invention comprises an opioid analgesic. In a non-limiting embodiment, an opioid analgesic useful in the pharmaceutical formulation can be selected from alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, a fentanyl derivative, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts of any of the foregoing, and the Like. In certain embodiments, the amount of the opioid analgesic in the dosage form of the pharmaceutical formulation may be from about 75 ng to about 750 mg. The opioid analgesic may be in immediate release or controlled release form.

In certain preferred embodiments, the opioid analgesic is selected from the group consisting of hydrocodone, morphine, hydromorphone, oxycodone, codeine, levorphanol, meperidine, methadone, oxymorphone, buprenorphine, fentanyl, a fentanyl derivative, dipipanone, heroin, tramadol, etorphine, dihydroetorphine, butorphanol, levorphanol, salts thereof and mixtures thereof. In certain preferred embodiments, the opioid analgesic is oxycodone or hydrocodone or salts thereof.

Certain other drugs which are useful in accordance with the present invention, include for example and without limitation, alimentary drugs; anti-infectives (e.g., antibiotics; antifungals; anti-virals such as anti-HIV/AIDS and anti-herpes; and anti-malarials); cardiovascular drugs (e.g., ace inhibitors; and cholesterol lower drugs such as the statins (e.g., Lipitor®)); CNS drugs (e.g., SSRIs such as Zoloft®, Prozac®, Effexor®, Lexapro®; anti-anxiolytics such as benzodiazepines; stimulants such as Ritalin®); dermatological drugs; genito-urinary drugs; hormones (e.g., anabolic steroids; growth hormone; and estrogen); life style drugs (e.g., drugs for treating erectile dysfunction such as Viagra®, Levitra®; drugs for treating hair loss such as Propecia®); musculoskeletal drugs; and respiratory drugs.

The following descriptions are for exemplification purposes only and examples are not meant to limit the invention in any manner.

Referring to the drawings, and initially to FIG. 1, a conventional pharmaceutical container is illustrated which has a threaded neck 11 to which a cap 12 can be threadedly engaged to keep the neck sealed. Threaded neck 11 has a spiral thread formed on it which engages one or more complementary threads formed on the inner surface of the cap 12. Additionally, neck 11 has an annular ring or flange 13 projecting from it which engages a complementary inwardly projecting ring on the bottom of cap 12 that is secured to the base of the cap in a well known manner. In accordance with this embodiment, a layer of material 14 containing microencapsulated aroma is applied to the underside of flange 13 on neck 11. Preferably, the microencapsulated material 14 is applied to flange 13 as a slurry and allowed to dry. When the bottle is opened by turning the cap the microcapsules burst and release the aroma.

Figure 2:
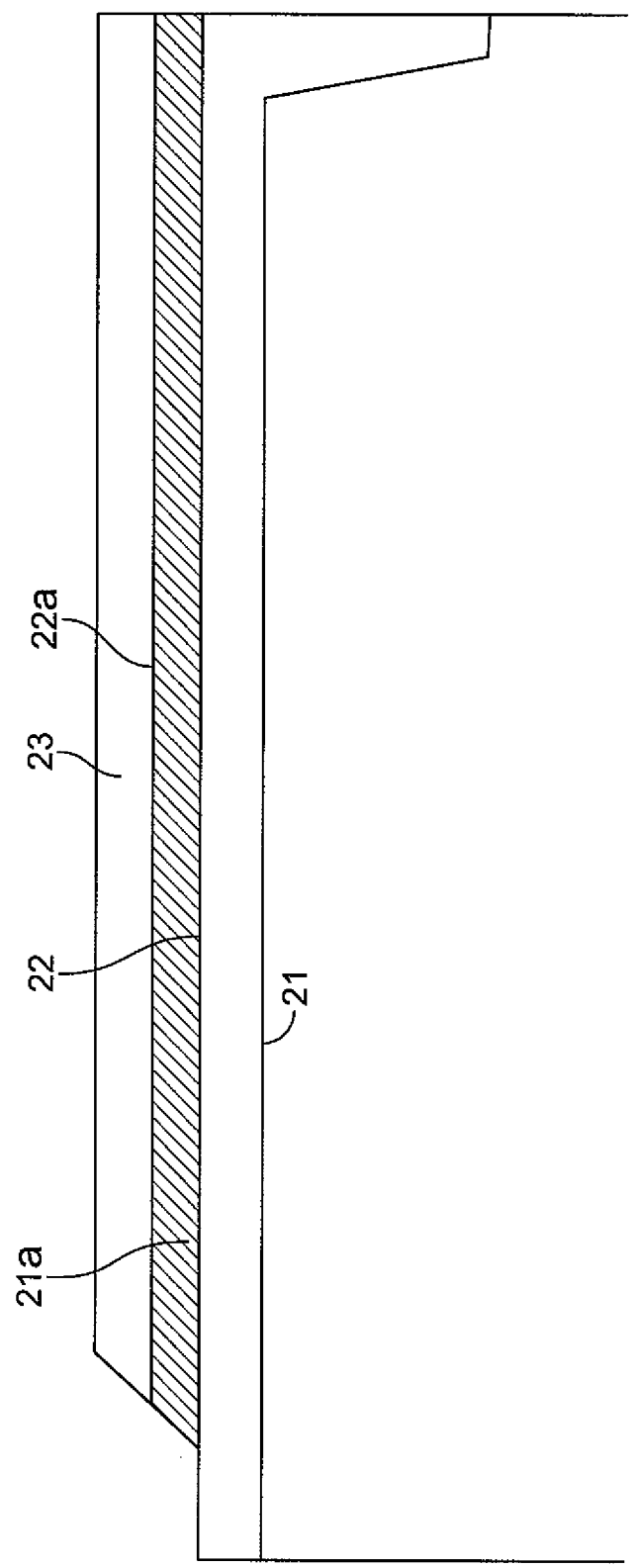
FIG. 2 depicts a pharmaceutical packaging system which includes a scent in accordance with the present invention.

FIG. 2 is a cross-sectional view of overlapping flaps of a pharmaceutical packaging system which includes the base flap 21, face 21a of which is overcoated with layer 22 comprising a scent and adhesive, and flap 23, which contacts surface 22a. When flap 23 is removed, it causes the scent in layer 22 to be released.

Example 1

In this prophetic example, hydrocodone sustained release tablets are produced with the formula set forth in Table 1 below:

TABLE 1

| Ingredients | Amt/Unit (mg) | Amount/Batch (gm) |
| --- | --- | --- |
| Hydrocodone Bitartrate | 15.0 | 150.0 |
| Spray Dried Lactose | 56.0 | 560.0 |
| Povidone | 4.0 | 40.0 |
| Eudragit RS30D (solids) | 10.0 | 100.0 |
| Triacetin | 2.0 | 20.0 |
| Stearyl Alcohol | 20.0 | 200.0 |
| Talc | 2.0 | 20.0 |
| Magnesium Stearate | 1.0 | 10.0 |
| Total | 110.0 | 1100.0 |

According to the following procedure:
1. Retardant dispersion: Blend Eudragit RS30D and Triacetin using a lightning mixer.
2. Melt Stearyl Alcohol.
3. Spray retardant dispersion onto Hydrocodone Bitartrate, Spray Dried Lactose, and Povidone using a fluid bed granulator.
4. Dry batch on a stainless steel tray for 15 minutes, or till constant weight.
5. Incorporate the melted Stearyl Alcohol into the batch using a Hobart mixer.
6. Dry waxed granulation on a stainless steel tray for 30 minutes, or temperature of granulation reaches 35° C. or less.
7. Mill the cooled granulation through a CoMil.
8. Lubricate the granulation with talc and magnesium stearate using a Hobart Mixer.
9. Compress the granulation into tablets using a tablet press.

The tablets are then coated with an aqueous film coating which is prepared by, e.g., dispersing 5.0 gm Opadry Purple YS-1-10371-A (per batch) and an amount of decanal in purified water and applying it to the tablet cores. The amount of decanal can be in an amount above the human threshold, or below the human threshold, but in an amount to be detectable by an electronic nose. The amount of decanal to obtain the desired threshold can be determined by one skilled in the art, e.g., by reference to page 51 of M. Devos, et al., *Standardized Human Olfactory Thresholds*, 1990.

Example 2

Scented Sequestered Naltrexone

In this prophetic example, the opioid antagonist naltrexone HCl is formulated as a melt extruded multiparticulates (hereinafter "MEMs") to produce a sequestered product. The formula is listed in the table below.

TABLE 2

| Ingredient | Amt/unit (mg) | Amt/batch (kg) |
|---|---|---|
| Naltrexone HCl | 2.0 | 0.10 |
| Eudragit RSPO | 88.0 | 4.40 |
| Stearyl Alcohol | 15.0 | 0.75 |
| Stearic Acid | 15.0 | 0.75 |
| Butylated Hydroxytoluene (BHT) | 1.0 | 0.05 |
| Total | 121.0 | 6.05 |

The naltrexone HCl formulation of Example 1 is prepared using the following process:

Process

1. Milling: Pass the stearyl alcohol flakes through an oscillating mill equipped with a 16 mesh screen to achieve a powder that is easily blendable.
2. Blending: Mix Naltrexone HCl, Eudragit RSPO, milled Stearyl Alcohol, Stearic Acid and BHT in a twin shell blender.
3. Extruding: Continuously feed the blended material from Step 2 into a twin screw extruder and collect extruded (Leistritz ZSE-27) at a rate ranging from 1.7 kg/hr to 2.6 kg/hr. Extrude the blend at a barrel temperature range of 75° C. and 100° C. into strands approximately 1 mm in diameter. Collect the extruded strands on a conveyor.
4. Coolin: Allow the strands to cool on the conveyor.
5. Pelletizing: Cut the cooled strands into pellets approximately 1 mm in length using a Pelletizer.
6. Screening: Screen the pellets through a vibratory separator using a 16 TBC mesh and a 26 TEC mesh screen. Collect the material retained on the 26 TBC mesh screen as desired product.
7. Encapsulating: Fill the screened pellets into hard gelatin capsules at a target weight of 121 mg.

An amount of benzaldehyde is included in the above process in the blending and/or the extruding step.

The scented MEMs are then coated with a 25% coating of acrylic polymer as follows:

Table 2A

| Coated Pellet Formula for 25% Weight Gain | | |
|---|---|---|
| Ingredient | Amt/unit (mg) | Amt/batch (kg) |
| Scented Naltrexone HCl Pellets | 121.0 | 0.50 |
| Eudragit RS30D (solids) | 30.25 | 0.125 |
| TriEthyl Citrate | 6.05 | 0.025 |
| Cab-O-Sil | 1.5 | 0.0062 |
| Opadry Pink | 6.0 | 0.025 |
| Total | 164.8 | 0.68 |

The coating is prepared according to the following process:

Process

1. Functional Coating Dispersion: Mix Eudragit RS 30D with triethyl citrate to plasticize for 15 minutes. Disperse Cab-O-Sil in enough water to achieve a total of 20% w/w solids dispersion. Add the Cab-O-Sil dispersion to the Eudragit mixture.
2. Color Coating Dispersion: Mix Opadry with water to get a 10% w/w dispersion.
3. Functional Coating: Spray the Eudragit dispersion onto the Naltrexone pellets prepared above at 700 g scale using a fluid bed processor (GPCG-1) with the following parameter guidelines:
   Air Speed: 8.5 to 9.5 m/s
   Inlet Air Temperature: 35° C.
   Dispersion Spray Rate: 14 g/min
   Samples were taken at when the theoretical amount of dispersion was sprayed for 5%, 10%, 15%, 20%, and 25% weight gain.
4. Color Coating: Upon completion of the functional coating, spray Opadry dispersion onto the coated pellets using the following parameter guidelines:
   Air Speed: 8.5 m/s
   Inlet Air Temperature: 35-45° C.
   Dispersion Spray Rate: 8.5 g/min
5. Screening: Screen the pellets through a 14 US mesh screen and a 20 US mesh screen. Collect the material retained on the 20 US mesh screen as desired product.
6. Curing: Place the screened pellets and samples in an oven at 45° C. for 24 hours.

Upon crushing with a mortar and pestel, it is expected that a "burst" of scent will be released which can facilitate the detection of the scent, e.g., by a human olfactory sytem, a non-human mammalian animal, or an olfactory measuring device, or a combination thereof. The amount of decanal to obtain the desired threshold can be determined by one skilled in the art, e.g., by reference to page 28 of M. Devos, et al., *Standardized Human Olfactory Thresholds*, 1990.

In an alternate embodiment, a second scent, e.g. decanal, can be included in the color coating of step 4 in a similar manner as in Example 1.

While the invention herein disclosed has been described by means of specific embodiments and applications thereof, numerous modifications and variations could be made thereto by those skilled in the art without departing from the spirit and scope of the present invention. Such modifications are understood to be within the scope of the appended claims.

What is claimed is:

1. A pharmaceutical formulation comprising a drug and an imparted volatile scent, wherein the scent comprises less than 100 ppm of the dosage form, provides an olfactory effect which is physiologically unperceivable by humans, is detectable by a non-human animal or an electronic olfactory measuring device, excludes perfluorocarbon tracers, and indicates when and/or where the pharmaceutical formulation was manufactured, bottled or packaged, and the pharmaceutical formulation is a tablet or a capsule.

2. The pharmaceutical formulation of claim 1, wherein the amount of the scent is detectable by the electronic olfactory measuring device.

3. The pharmaceutical formulation of claim 1, wherein the scent indicates where the pharmaceutical formulation was manufactured, bottled or packaged.

4. The pharmaceutical formulation of claim 1 comprising a coating.

5. The pharmaceutical formulation of claim 4, wherein the coating is a film coating.

6. The pharmaceutical formulation of claim 4, wherein the coating comprises the scent.

7. The pharmaceutical formulation of claim 1, wherein the scent is sequestered.

8. The pharmaceutical formulation of claim 1, wherein the scent comprises a plurality of scents.

9. A pharmaceutical formulation comprising an opioid and an imparted volatile scent, wherein the scent comprises less than 100 ppm of the dosage form, provides an olfactory effect which is physiologically unperceivable by humans, is detectable by a non-human animal or an electronic olfactory measuring device, excludes perfluorocarbon tracers, and indicates when and/or where the pharmaceutical formulation was manufactured, bottled or packaged.

10. The pharmaceutical formulation of claim 9, wherein the amount of the scent is detectable by the electronic olfactory measuring device.

11. The pharmaceutical formulation of claim 9, wherein the scent indicates where the pharmaceutical formulation was manufactured, bottled or packaged.

12. The pharmaceutical formulation of claim 9 comprising a coating.

13. The pharmaceutical formulation of claim 12, wherein the coating is a film coating.

14. The pharmaceutical formulation of claim 12, wherein the coating comprises the scent.

15. The pharmaceutical formulation of claim 9, wherein the scent is sequestered.

16. The pharmaceutical formulation of claim 9, wherein the scent comprises a plurality of scents.

17. The pharmaceutical formulation of claim 9 which is a tablet or a capsule.

18. The pharmaceutical formulation of claim 1, wherein the scent is selected from the group consisting of volatile oils, synthetic flavor oils, flavoring aromatics, natural flavor oils, flavoring liquid oleoresins, flower extracts, fruit extracts, and combinations thereof.

19. The pharmaceutical formulation of claim 1, wherein the scent is selected from the group consisting of aldehydes, esters and mixtures thereof.

20. The pharmaceutical formulation of claim 1, wherein the scent is selected from the group consisting of anise, apple, arnica, balm mint, banana, basil, black pine, caraway, carnation, chamomile, cherry, Chinese cedar wood, chocolate, cinnamon, coconut, coffee, cypress, dill weed, eucalyptus, fir, fleurier, florogenia, forest ground, fresh baked bread, ginger bread, green apple, green bean, green spruce, hay flower, hazel, honey, hyacinth, incense, jacilia, jasmine, juniper, keymi, lavender, leather, lemon, lilac, lotus, mandarin, mango, maracuja, marjoram, May-flower, menthol, mixed alpine herbs, mugol, northern birch, ocean breeze, orange, orchid, ozone pine, peach, pear, petunias, pine, pinewood, pink pepper, pizza, plum, rose, raspberry, rosemary, sandalwood, sea breeze, Siberian spruce, spring, spruce pine, strawberry, thyme, tobacco, tomato, valerian, vanilla, violet, waffle, wild woodberry, musk, and mixtures thereof.

21. The pharmaceutical formulation of claim 1, wherein the scent is selected from the group consisting of a fatty acid with short chains of two to six carbon atoms, ketones, aldehydes, amines, o- and p-hydoxy benzoic acids and their esters, and combinations thereof.

22. The pharmaceutical formulation of claim 9, wherein the scent is selected from the group consisting of volatile oils, synthetic flavor oils, flavoring aromatics, natural flavor oils, flavoring liquid oleoresins, flower extracts, fruit extracts, and combinations thereof.

23. The pharmaceutical formulation of claim 9, wherein the scent is selected from the group consisting of aldehydes, esters and mixtures thereof.

24. The pharmaceutical formulation of claim 9, wherein the scent is selected from the group consisting of anise, apple, arnica, balm mint, banana, basil, black pine, caraway, carnation, chamomile, cherry, Chinese cedar wood, chocolate, cinnamon, coconut, coffee, cypress, dill weed, eucalyptus, fir, fleurier, florogenia, forest ground, fresh baked bread, ginger bread, green apple, green bean, green spruce, hay flower, hazel, honey, hyacinth, incense, jacilia, jasmine, juniper, keymi, lavender, leather, lemon, lilac, lotus, mandarin, mango, maracuja, marjoram, May-flower, menthol, mixed alpine herbs, mugol, northern birch, ocean breeze, orange, orchid, ozone pine, peach, pear, petunias, pine, pinewood, pink pepper, pizza, plum, rose, raspberry, rosemary, sandalwood, sea breeze, Siberian spruce, spring, spruce pine, strawberry, thyme, tobacco, tomato, valerian, vanilla, violet, waffle, wild woodberry, musk, and mixtures thereof.

25. The pharmaceutical formulation of claim 9, wherein the scent is selected from the group consisting of a fatty acid with short chains of two to six carbon atoms, ketones, aldehydes, amines, o- and p-hydoxy benzoic acids and their esters, and combinations thereof.

* * * * *